United States Patent
Hao et al.

(10) Patent No.: US 6,984,211 B2
(45) Date of Patent: Jan. 10, 2006

(54) DETECTION OF TUMOR HALOS IN ULTRASOUND IMAGES

(75) Inventors: Xiaohui Hao, Waukesha, WI (US); Joseph William Charboneau, Rochester, MN (US); Nicholas James Hangiandreou, Rochester, MN (US); James Fowler Greenleaf, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 159 days.

(21) Appl. No.: 10/751,151

(22) Filed: Jan. 2, 2004

(65) Prior Publication Data

US 2004/0199077 A1    Oct. 7, 2004

Related U.S. Application Data

(60) Provisional application No. 60/438,010, filed on Jan. 3, 2003.

(51) Int. Cl.
*A61B 8/00* (2006.01)

(52) U.S. Cl. .................................................. 600/443
(58) Field of Classification Search ............... 600/437, 600/440–443, 447; 128/916; 382/128–134, 382/171–173, 180, 266, 274, 288
See application file for complete search history.

(56) References Cited

U.S. PATENT DOCUMENTS

| | | | | | |
|---|---|---|---|---|---|
| 5,224,175 | A | * | 6/1993 | Gouge et al. | 382/128 |
| 5,260,871 | A | * | 11/1993 | Goldberg | 600/320 |
| 6,154,560 | A | * | 11/2000 | Cothren et al. | 382/128 |
| 6,292,682 | B1 | * | 9/2001 | Kruger | 600/407 |
| 6,312,385 | B1 | * | 11/2001 | Mo et al. | 600/443 |
| 6,901,277 | B2 | * | 5/2005 | Kaufman et al. | 600/407 |
| 2003/0086608 | A1 | * | 5/2003 | Frost et al. | 382/173 |

* cited by examiner

Primary Examiner—Francis J. Jaworski
(74) Attorney, Agent, or Firm—Quarles & Brady LLP

(57) ABSTRACT

A halo surrounding the ultrasonic image of a liver tumor is automatically evaluated by detecting the boundary of the tumor and defining two annular regions around that boundary. The brightness of pixels in the two annular regions are compared to determine if a halo of darker pixels surround the tumor. Presence of this halo is indicative of a malignant tumor.

15 Claims, 5 Drawing Sheets

US 6,984,211 B2

DETECTION OF TUMOR HALOS IN ULTRASOUND IMAGES

CROSS-REFERENCE TO RELATED APPLICATIONS

This application claims the benefit of U.S. Provisional patent application Ser. No. 60/438,010 filed on Jan. 3, 2003 and entitled "DETECTION OF LIVER TUMOR HALOS IN ULTRASOUND IMAGES".

BACKGROUND OF THE INVENTION

The field of the invention is clinical ultrasonic imaging, and particularly the processing of ultrasonic images to derive clinical information.

There are a number of modes in which ultrasound can be used to produce images of objects. The ultrasound transmitter may be placed on one side of the object and the sound transmitted through the object to the ultrasound receiver placed on the other side ("transmission mode"). With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("refraction", "backscatter" or "echo" mode). The present invention relates to a backscatter method for producing ultrasound images.

There are a number of well known backscatter methods for acquiring ultrasound data. In the so-called "A-scan" method, an ultrasound pulse is directed into the object by the transducer and the amplitude of the reflected sound is recorded over a period of time. The amplitude of the echo signal is proportional to the scattering strength of the refractors in the object and the time delay is proportional to the range of the refractors from the transducer. In the so-called "B-scan" method, the transducer transmits a series of ultrasonic pulses as it is scanned across the object along a single axis of motion. The resulting echo signals are recorded as with the A-scan method and either their amplitude or time delay is used to modulate the brightness of pixels on a display. With the B-scan method, enough data are acquired from which an image of the reflectors can be reconstructed.

In the so-called C-scan method, the transducer is scanned across a plane above the object and only the echoes reflecting from the focal depth of the transducer are recorded. The sweep of the electron beam of a CRT display is synchronized to the scanning of the transducer so that the x and y coordinates of the transducer correspond to the x and y coordinates of the image.

Ultrasonic transducers for medical applications are constructed from one or more piezoelectric elements sandwiched between a pair of electrodes. Such piezoelectric elements are typically constructed of lead zirconate titanate (PZT), polyvinylidene difluoride (PVDF), or PZT ceramic/polymer composite. The electrodes are connected to a voltage source, and when a voltage is applied, the piezoelectric elements change in size at a frequency corresponding to that of the applied voltage. When a voltage pulse is applied, the piezoelectric element emits an ultrasonic wave into the media to which it is coupled at the frequencies contained in the excitation pulse. Conversely, when an ultrasonic wave strikes the piezoelectric element, the element produces a corresponding voltage across its electrodes. Typically, the front of the element is covered with an acoustic matching layer that improves the coupling with the media in which the ultrasonic waves propagate. In addition, a backing material is disposed to the rear of the piezoelectric element to absorb ultrasonic waves that emerge from the back side of the element so that they do not interfere. A number of such ultrasonic transducer constructions are disclosed in U.S. Pat. Nos. 4,217,684; 4,425,525; 4,441,503; 4,470,305 and 4,569,231.

When used for ultrasound imaging, the transducer typically has a number of piezoelectric elements arranged in an array and driven with separate voltages (apodizing). By controlling the time delay (or phase) and amplitude of the applied voltages, the ultrasonic waves produced by the piezoelectric elements (transmission mode) combine to produce a net ultrasonic wave focused at a selected point. By controlling the time delay and amplitude of the applied voltages, this focal point can be moved in a plane to scan the subject.

The same principles apply when the transducer is employed to receive the reflected sound (receiver mode). That is, the voltages produced at the transducer elements in the array are summed together such that the net signal is indicative of the sound reflected from a single focal point in the subject. As with the transmission mode, this focused reception of the ultrasonic energy is achieved by imparting separate time delay (and/or phase shifts) and gains to the signal from each transducer array element.

This form of ultrasonic imaging is referred to as "phased array sector scanning", or "PASS". Such a scan is comprised of a series of measurements in which the steered ultrasonic wave is transmitted, the system switches to receive mode after a short time interval, and the reflected ultrasonic wave is received and stored. Typically, the transmission and reception are steered in the same direction (θ) during each measurement to acquire data from a series of points along a scan line. The receiver is dynamically focused at a succession of ranges (R) along the scan line as the reflected ultrasonic waves are received. The time required to conduct the entire scan is a function of the time required to make each measurement and the number of measurements required to cover the entire region of interest at the desired resolution and signal-to-noise ratio. For example, a total of 128 scan lines may be acquired over a 90 degree sector, with each scan line being steered in increments of 0.70°. A number of such ultrasonic imaging systems are disclosed in U.S. Pat. Nos. 4,155,258; 4,155,260; 4,154,113; 4,155,259; 4,180,790; 4,470,303; 4,662,223; 4,669,314 and 4,809,184.

A characteristic of ultrasound images is that they contain speckle noise and attenuation artifacts. In addition, objects in the beam path can partially obscure the region of interest or attenuate the echo signals from a portion of the region of interest. As a result, experts are often required to extract clinical information from ultrasound images because the images cannot be automatically analyzed.

An example of such a situation is an ultrasound image of a subject's liver. It is known that when certain liver tumors are imaged with ultrasound, a band, or "halo" of diminished brightness surrounds the tumor when it is malignant. The halo is slightly darker than the surrounding healthy liver tissue, but there may be very little difference in some locations and no clear boundary. The presence of a halo around a liver tumor has been found to accurately predict malignancy or non-malignancy with an 87% accuracy, but expert radiologists are required to derive this clinical information from typical ultrasound images.

SUMMARY OF THE INVENTION

The present invention is a method for processing an ultrasonic image to detect the presence of a halo around a tumor. More specifically, the method includes: pre-filtering the ultrasonic image to enhance the detection of edges; locating the boundary of the tumor; defining a first annular region surrounding the tumor and adjacent to the tumor boundary; defining a second annular region surrounding the tumor and adjacent to the first annular region; and determining if the tumor is malignant or not by comparing the brightness of pixels in the first annular region with the brightness of pixels in the second annular region.

A general object of the invention is to simplify the task of determining if a tumor is clinically significant (usually malignant) or not based on an ultrasonic image of the tumor and surrounding tissues. The steps of the method can be preformed by a processor automatically with little or no human assistance. Even if human judgment is employed to assist in locating the tumor boundary, the task does not need the skill of an expert physician. We found that when the tumor edge was detected manually, the tumors in the testing set of data with an without halos were separated with 100% specificity and 100% sensitivity. When the tumor edge was detected semi-automatically, halos were detected with a specificity of 93%, and a sensitivity of 100%.

DETAILED DESCRIPTION OF THE PREFERRED EMBODIMENT

Figure 1:
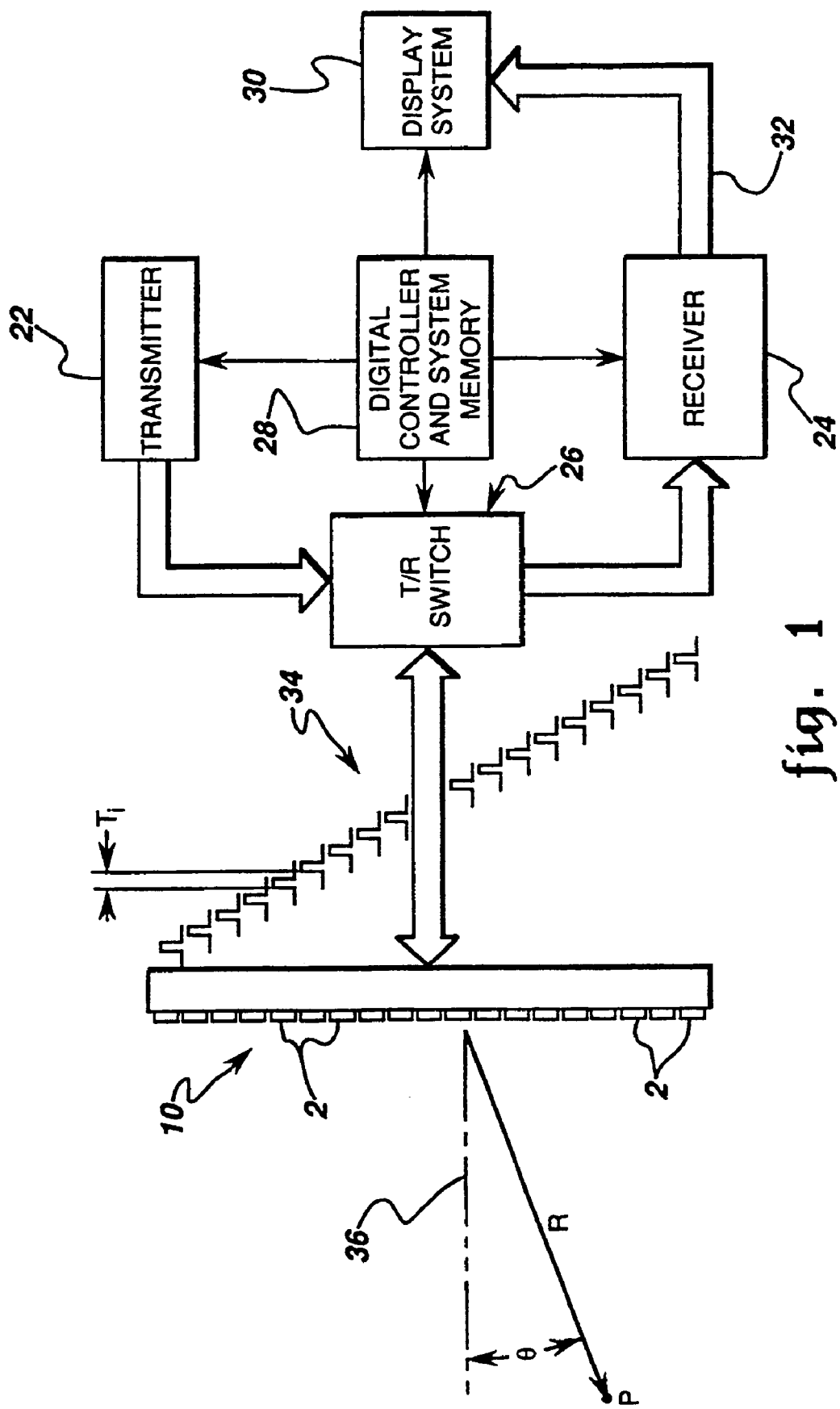
FIG. 1 is a block diagram of an ultrasound imaging system used to acquire an image processed by the present invention.

Referring particularly to FIG. 1, an ultrasonic imaging system includes a transducer array 11 comprised of a plurality of separately driven elements 12 which each produce a burst of ultrasonic energy when energized by a pulse produced by a transmitter 13. The ultrasonic energy reflected back to the transducer array 11 from the subject under study is converted to an electrical signal by each transducer element 12 and applied separately to a receiver 14 through a set of switches 15. The transmitter 13, receiver 14 and the switches 15 are operated under the control of a digital controller 16 responsive to the commands input by the human operator. A complete scan is performed by acquiring a series of echoes in which the switches 15 are set to their transmit position, the transmitter 13 is gated on momentarily to energize each transducer element 12, the switches 15 are then set to their receive position, and the subsequent echo signals produced by each transducer element 12 are applied to the receiver 14. The separate echo signals from each transducer element 12 are combined in the receiver 14 to produce a single echo signal which is employed to produce a line in an image on a display system 17.

The transmitter 13 drives the transducer array 11 such that the ultrasonic energy produced is directed, or steered, in a beam. A B-scan can therefore be performed by moving this beam through a set of angles from point-to-point rather than physically moving the transducer array 11. To accomplish this the transmitter 13 imparts a time delay (Ti) to the respective pulses 20 that are applied to successive transducer elements 12. If the time delay is zero (Ti=0), all the transducer elements 12 are energized simultaneously and the resulting ultrasonic beam is directed along an axis 21 normal to the transducer face and originating from the center of the transducer array 11. As the time delay (Ti) is increased as illustrated in FIG. 1, the ultrasonic beam is directed downward from the central axis 21 by an angle $\theta$.

A sector scan is performed by progressively changing the time delays Ti in successive excitations. The angle $\theta$ is thus changed in increments to steer the transmitted beam in a succession of directions. When the direction of the beam is above the central axis 21, the timing of the pulses 20 is reversed.

Referring still to FIG. 1, the echo signals produced by each burst of ultrasonic energy emanate from reflecting objects located at successive positions (R) along the ultrasonic beam. These are sensed separately by each segment 12 of the transducer array 11 and a sample of the magnitude of the echo signal at a particular point in time represents the amount of reflection occurring at a specific range (R). Due to the differences in the propagation paths between a focal point P and each transducer element 12, however, these echo signals will not occur simultaneously and their amplitudes will not be equal. The function of the receiver 14 is to amplify and demodulate these separate echo signals, impart the proper time delay to each and sum them together to provide a single echo signal which accurately indicates the total ultrasonic energy reflected from each focal point P located at range R along the ultrasonic beam oriented at the angle $\theta$.

Under the direction of the digital controller 16, the receiver 14 provides delays during the scan such that the steering of the receiver 14 tracks with the direction of the beam steered by the transmitter 13 and it samples the echo signals at a succession of ranges and provides the proper delays to dynamically focus at points P along the beam. Thus, each emission of an ultrasonic pulse results in the acquisition of a series of data points which represent the amount of reflected sound from a corresponding series of points P located along the ultrasonic beam.

The display system 17 receives the series of data points produced by the receiver 14 and converts the data to a form producing the desired image. For example, if an A-scan is desired, the magnitude of the series of data points is merely graphed as a function of time. If a B-scan is desired, each data point in the series is used to control the brightness of a pixel in the image, and a scan comprised of a series of measurements at successive steering angles ($\theta$) is performed to provide the data necessary for display.

The image produced by the ultrasound system is a two-dimensional array of digital values which indicate the brightness of a corresponding array of pixels in the acquired image. The processing required to implement the present invention could be performed in a suitably modified ultrasound system. Such a modification might include the addition of software, or the addition of DSP or ASIC hardware that is dedicated to this processing. The digital image may also be transferred to a separate processor for carrying out the processing according to the present invention. One such processor is shown in FIGS. 6 and 7, although it can be appreciated that any post processing workstation for medical image processing may be used.

Figure 6:
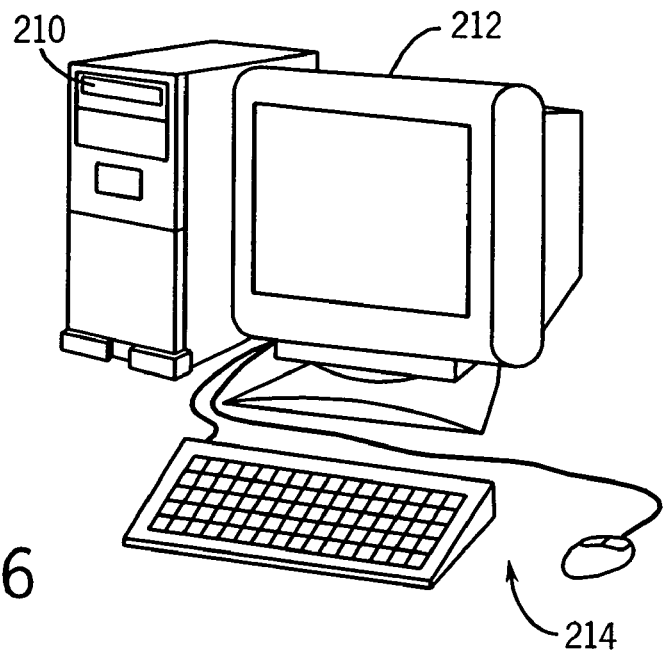
FIG. 6 is a pictorial representation of a work station that processes an ultrasonic image in accordance with the method of the present invention.

Referring particularly to FIG. 6, the workstation includes a mini-tower 210 which houses a processor and associated circuitry, memory, and peripheral interface circuits. One of the peripheral devices is a commercially available CRT monitor 212 which connects to a graphics circuit housed in the mini-tower 210, and another peripheral device is a keyboard and mouse 214 that connects to a PCI-based controller in the mini-tower 210. An operator may input data through the keyboard and control the position of a cursor on the monitor display 212 using the mouse.

Figure 7:
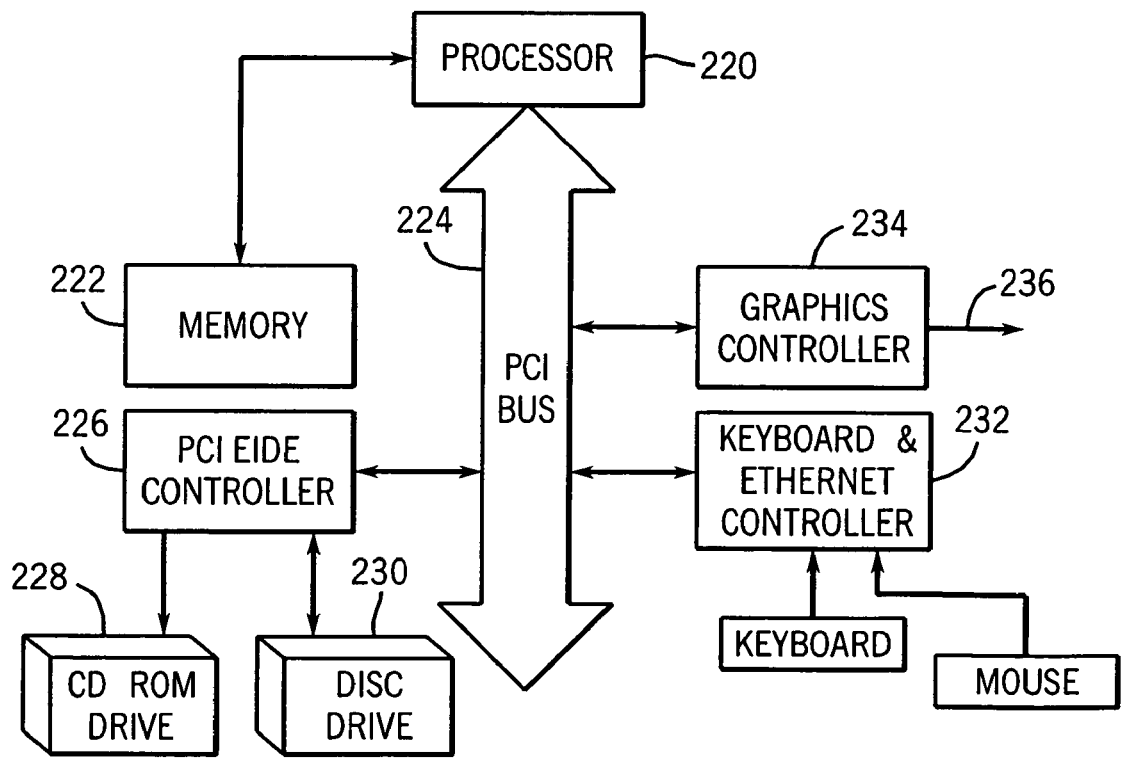
FIG. 7 is a block diagram of the workstation of FIG. 6.

Referring particularly to FIG. 7, the workstation includes a processor 220 which executes program instructions stored in a memory 222. The processor 220 is a commercially available device such as that sold by Sun Microsystems, Inc. under the trademark UltraSPARC-IIi. It incorporates on-chip memory and I/O control to facilitate system integration. It is a superscalar processor implementing the SPARC-V9 64-bit RISC architecture and executing the instruction set sold commercially under the trademark "VIS". It also includes an integral PCI bus driver which provides a direct interface with a 32-bit PCI bus 224. It also includes integral memory management circuitry for handling all external memory 222. Other general-purpose computers can be used, such as computers based on Intel, Advanced Micro Devices and Motorola microprocessors.

The PCI bus 224 is an industry standard bus that transfers 32-bits of data between the processor 220 and a number of peripheral controller cards. These include a PCI EIDE controller 226 which provides a high-speed transfer of data to and from a CD ROM drive 228 and a disc drive 230. An Ethernet controller 232 supports data transfer with a number of peripheral devices, including input from the keyboard and mouse 214 and communication with Ethernet ports. A graphics controller 34 couples the PCI bus 224 to the CRT monitor 212 through a standard VGA connection 236. Many other devices can be connected to the workstation using an appropriate PCI compatible interface circuit and associated driver software.

Figure 2:
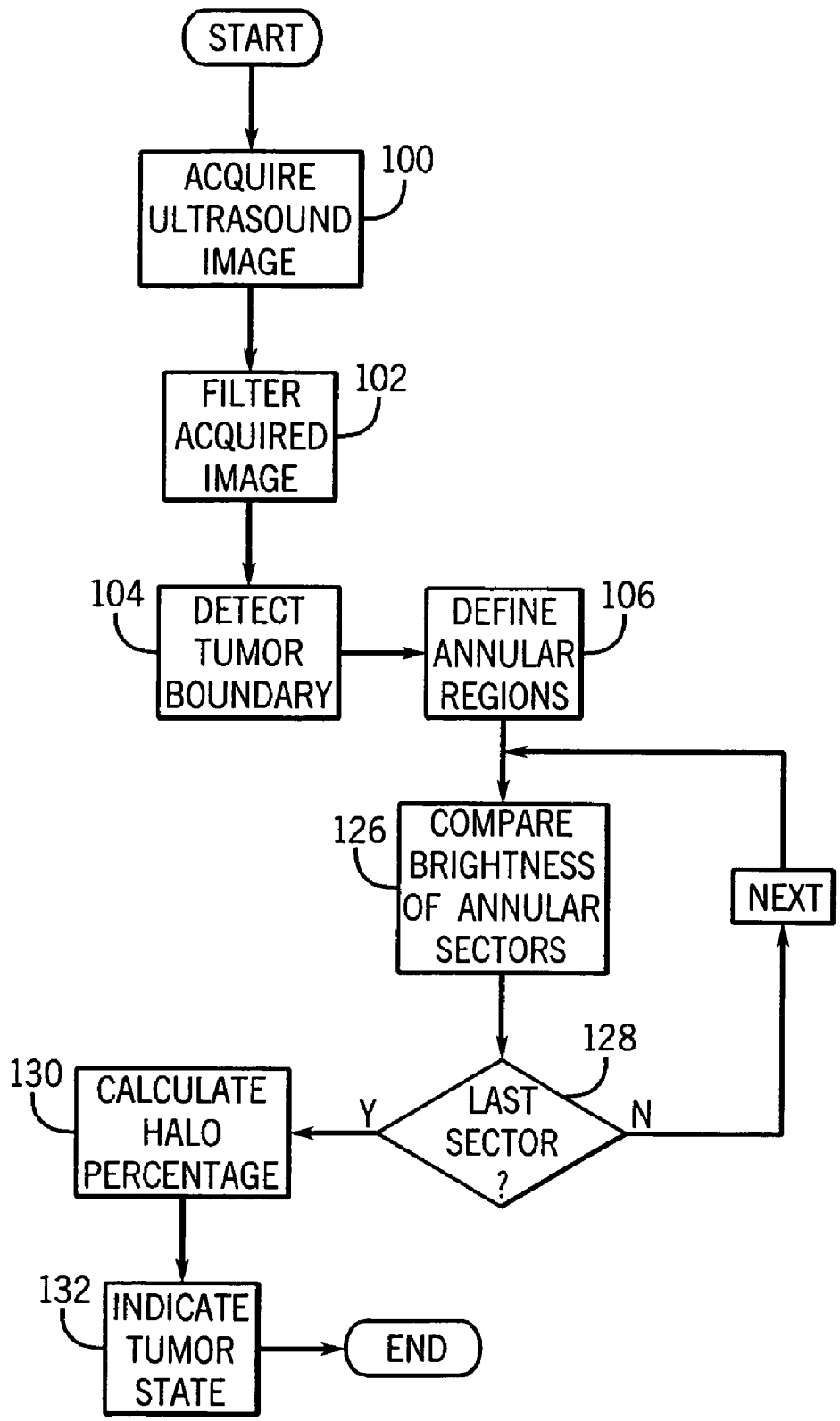
FIG. 2 is a flow chart of the steps in the preferred embodiment of the invented method.

Referring particularly to FIG. 2, the two-dimensional array of digital values which indicate the brightness of the acquired image is examined to detect the presence of a halo around a tumor depicted in the image. The acquired image is stored as indicated at process block 100 and is processed as will now be described.

Since ultrasound images are always corrupted by speckle noise and attenuation artifacts, filtering is done as indicated at process block 102 before edge finding. The filtering can be a speckle reduction processing, an edge enhancing processing, or a functional feature extraction. The functional feature may be elasticity parameters (e.g., Young's modulus, strain, strain rate, etc.) or a scatterer density parameter. The filtering can also be an image texture feature extraction process such as gray level run length, gray level co-occurrence matrix, local entropy, or local power spectrum. A local power spectrum method is employed in the preferred embodiment and it uses a 2d FFT of a M×M running window centered at pixel (i,j) of the image. It is defined as:

$$P(u,v)=|F^{(i,j)}(u,v)|^2, u,v=0,1,2,\ldots,M-1 \tag{1}$$

$$F^{(i,j)}(u,v)=FFT2(W_M^{i,j}) \tag{2}$$

where $W_M^{i,j}$ is the M×M window at the image pixel location (i,j).

The texture feature used is the maximum energy in the whole frequency band of the local window:

$$ME=\max(P(u,v)), u,v=0,1,2,\ldots,M-1 \tag{3}$$

The resulting filtered image is used to calculate the image features for edge finding.

As indicated at process block 104, the next step is to locate the boundary or edge, of the tumor depicted in the filtered image. This can be done in a number of ways and in the preferred embodiment the user has a choice of a manual method or a semiautomatic method. With the manual method the user operates the mouse to designate with a cursor a number of points on the tumor boundary displayed on the screen 212. More than 15 points are usually required to adequately define the boundary. The designated points are connected together with straight lines to form a polygon that defines the tumor edge. In the alternative, the cursor can be moved around the tumor boundary while depressing a mouse button to designate the entire tumor boundary path directly.

With the semi-automatic method the user manually designates the location of less than 10 points surrounding the tumor. These points do not need to be precisely on the edge. Any one of a number of edge finding methods may then be used to locate the tumor boundary. These include: dynamic contour; level set; or neural net based edge extraction methods. In the preferred embodiment we use a "snake" method to find the real edge as described by Kass M., Witkin A., Terzopoulos D., "Snakes: Active Contour Models", In the International Journal of Computer Vision, Vol. 1, 321–331, 1988. A snake is an energy-minimizing spline guided by external constraint forces and influenced by image forces that pull it toward features such as lines and edges. If the position of a snake is parametrically represented by $v_s=[x_s,y_s]$, its energy function can be written as:

$$E_{snake} = \int_0^1 [E_{int}(v_s) + E_{image}(v_s)]\,ds \tag{4}$$

The internal energy $E_{int}$ represents the forces which constrain the curve to be smooth, $E_{image}$ represents the forces derived from the image that constrain the curve to take the shape of the features (we use image gradients: $-|\nabla I(x,y)^2|$) present in the image. The edge is found by minimizing the total energy $E_{snake}$. The snake is deformed in a limited area $S_{annular}$ defined by a few selected points $[x_{in},y_{in}]$:

$$v_s=[x_s,y_s]\in S_{annular}(x_{in},y_{in}). \tag{5}$$

The limited area is acquired by first connecting the user-input points then expanding it outward from the tumor center and shrinking it toward the tumor center. The snakes are iteratively deformed to find the minimum of the total energy $E_{snake}$.

A fully automatic edge finding method may also be employed. In the fully automatic method, either there is no need for any input from the user or the only input from the user may be just to click on the tumor or designate the region of interest in the displayed image. Then an image segmentation method such as region growing, or edge extraction methods such as snakes, level set based method, neural network based edge finding method is employed to locate the tumor boundary.

Figure 3:
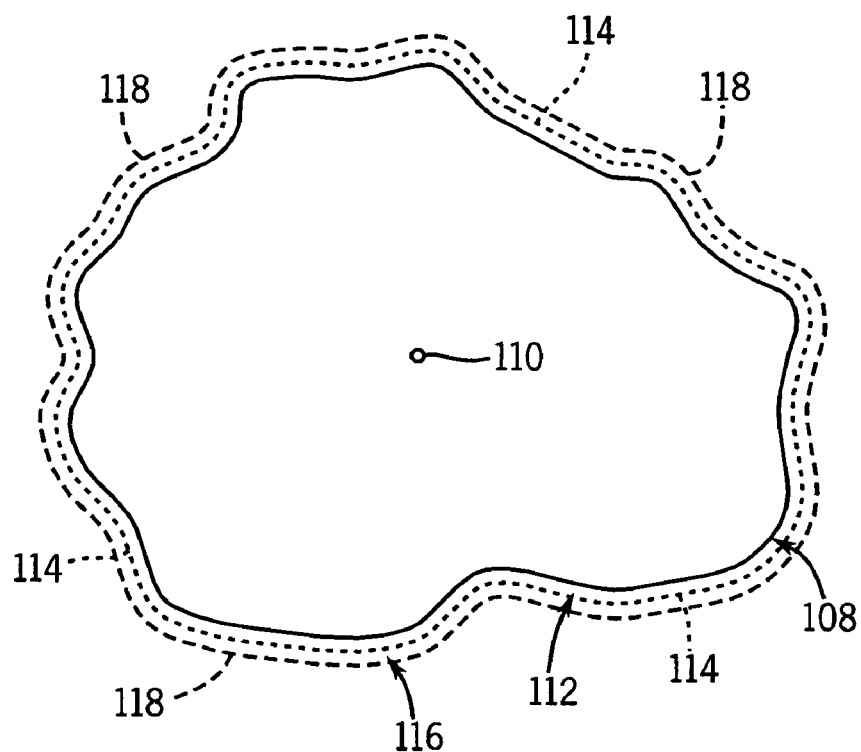
FIG. 3 is a pictorial representation of an imaged tumor after its boundary has been detected and annular regions have been defined around it in accordance with the teachings of the present invention.

After the tumor edge has been located two annular regions are defined around the tumor as indicated at process block 106. This step is best illustrated in FIG. 3, where the tumor edge is indicated at 108 and the center of the tumor is indicated at 110. A first, or inner, annular region 112 is defined by extending rays from the center 110 a preselected distance beyond the tumor edge to points indicated by dotted line 114. A second, or outer, annular region 116 is defined by extending these same rays a preselected distance beyond the outer boundary of the inner annular region 112 to points indicated by dashed line 118. The preselected distances that determine the size of the annular regions may be set in a number of different ways. The objective is to size the inner annulus 112 such that it is substantially coextensive with any halo that might be present. The outer annulus 116 is at least twice the size, but it samples, or overlies, pixels depicting normal liver tissues. First, a manual method can be used in which the user defines the size of the halo region as it appears on the displayed image. Second, the size of the halo region can be determined automatically by extending rays outward from the tumor boundary and examining the pixel brightness value. A reduction, or valley, in brightness values characterizes the halo and an average or median value of these measurements can be used to determine the inner annulus size. And third, the size of the inner annulus 112 may be set to a fixed value which has been determined empirically to work. In the preferred embodiment this last method is used and the preset value is 7 pixels. For all three methods, the size of the outer annular region 116 is set to at least two times the size of the inner annulus 112, and in the preferred embodiment it is set to 20 pixels.

Figure 4:
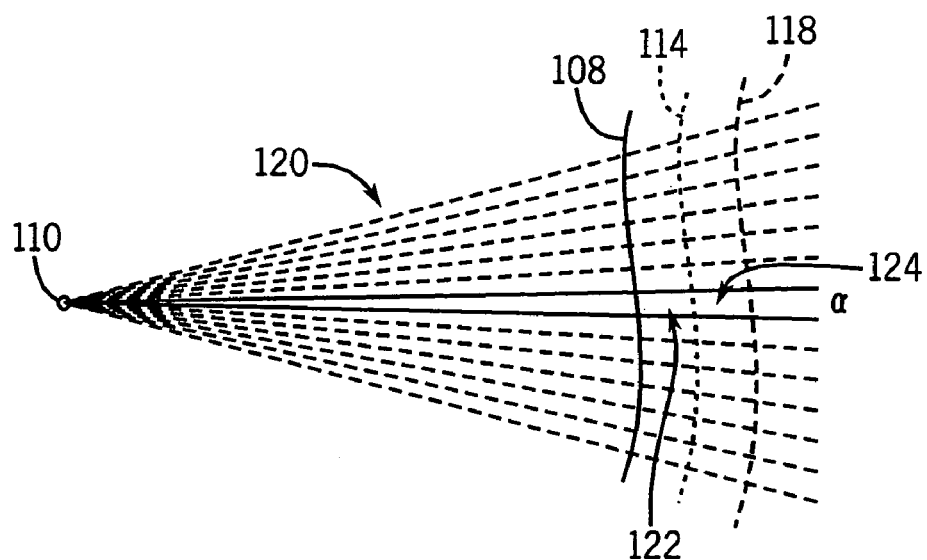
FIG. 4 is a pictorial view of a portion of the tumor boundary and annular regions of FIG. 3 divided into sectors.

Referring to FIG. 2, a loop is entered next in which the brightness of the two annular regions 112 and 116 is compared. As shown in FIG. 4, the annular regions 112 and 116 are first divided into 1° sectors by rays 120 that extend outward from the tumor center 110. At each sector α, the average gray level intensities within the interior sector 122 ($G\_int_\alpha$) and the exterior sector 124 ($G\_ext_\alpha$) are compared as indicated at process block 126. When the last sector has been compared, as indicated at decision block 128, the percentage of interior sectors 122 (hereinafter "halo_percentage") with average gray level intensity less than the average gray level intensity of the exterior sectors 124 is calculated as indicated at process block 130:

$$halo_\alpha \begin{cases} 1 & \text{if } G\_int_\alpha < G\_ext_\alpha, \\ 0 & \text{else} \end{cases} \quad (6)$$

$$halo\_percentage = \left(\sum_{\alpha=1}^{360} halo_\alpha\right) / 360 \times 100\%.$$

This halo_percentage is used to indicate the presence of a halo. The halo_percentage which is indicative of a clinically significant mass (usually a malignant tumor) has been determined empirically from experiments. Sixty-two in vivo images of hyper-echoic and iso-echoic liver tumors (size: 1~5 cm) were collected using an ultrasonic scanner manufactured by Acuson and sold under the model name "Sequoia". The images were captured either by DICOM transfer or by video digitization into a picture archive and communication system (PACS), and were irreversibly compressed using baseline JPEG with a nominal compression ratio of 9:1. A radiologist specializing in ultrasound visually evaluated and categorized the images according to the presence or absence of a peripheral hypo-echoic halo. Both complete and incomplete halos were represented. A total of 16 images with halo and 15 without were used as the training set for the method. Both the manual and the semi-automatic methods were employed for detecting the tumor edges.

Figure 5A:
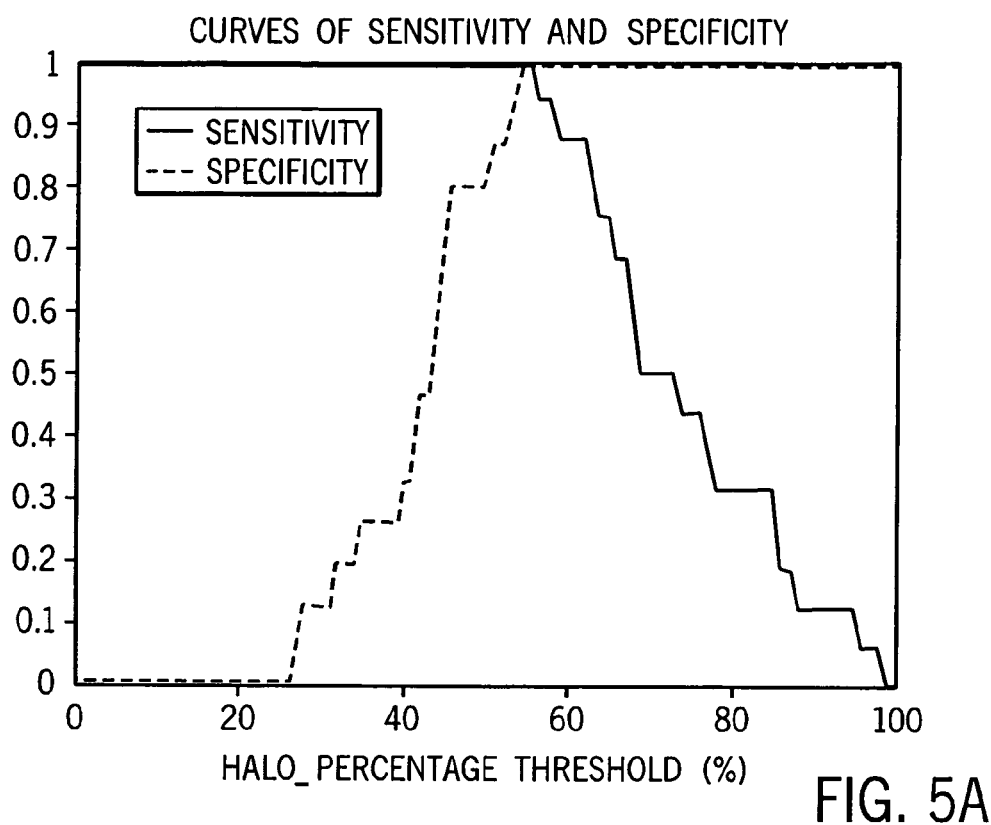
FIGS. 5A and 5B are graphs of sensitivity and specificity versus halo percentage when the present invention is employed with manual tumor boundary detection and semi-automatic tumor boundary detection respectively.
Figure 5B:
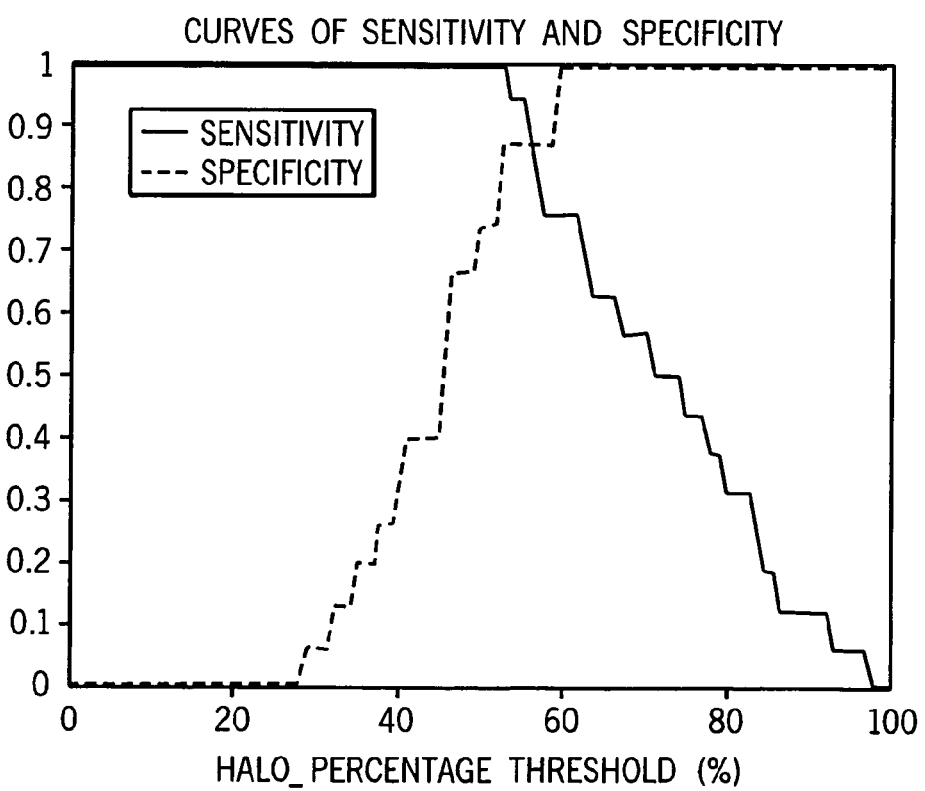

The halo_percentage value was calculated for each image as described above. The separating halo-percentage thresholds (one with manual edge finding, the other with semi-automatic edge finding) were found by maximizing the specificity while maintaining 100% sensitivity. The remaining 31 tumor images, which also consisted of 16 images with halo and 15 without halos, were used as the test set. From the training set, we found that the area below the ROC curve for the semi-automatic edge tracing is 0.9667 and the corresponding area for the manual tracing is 1. FIGS. 5A and 5B show the sensitivity and specificity curves for the training set with manual edge detection and semi-automatic edge detection, respectively. The optimal halo-percentage thresholds were found to be 53% and 51% for the manual and semi-automated methods, respectively.

As indicated at process block 132 in FIG. 2, if the calculated halo-percentage exceeds the 53% or 51% level, a halo is present and a probable malignant tumor is indicated.

It should be apparent to those skilled in the art that variations can be made from the preferred embodiment of the invention without departing from the spirit of the invention. For example, if a three-dimensional ultrasound image of the tumor is acquired the annular regions are three-dimensional and form a shell around the tumor boundary. The sectors in this embodiment of the invention are three-dimensional segments of these shells. Also, while pixel brightness, or magnitude, is the preferred image parameter that is measured and compared in the two annular regions, other image parameters such as variance or kurtosis of a small neighborhood of pixels may also be measured and compared. And finally, while the preferred embodiment of the invention has been applied to liver tumors, it is believed that the method may also be used as a diagnostic tool for other types of tumors.

The invention claimed is:

1. A method for detecting a halo surrounding an ultrasound image of a tumor, the steps comprising:
   a) locating the boundary of the tumor in the image;
   b) defining a first annular region surrounding the tumor and adjacent the tumor boundary;
   c) defining a second annular region surrounding the tumor and adjacent the first annular region; and
   d) determining the presence of a halo by comparing the value of an image parameter of image pixels in the first annular region with the value of the image parameter of pixels in the second annular region.

2. The method as recited in claim 1 which includes filtering the ultrasound image before performing step a).

3. The method as recited in claim 1 in which step d) includes:
   i) dividing the first and second annular regions into a plurality of sectors; and
   ii) comparing the average brightness of image pixels in each sector of the first annular region with the average brightness of image pixels in the corresponding sector in the second annular region.

4. The method as recited in claim 3 in which the presence of a halo is determined by the number of sectors in which the average brightness of the first annular region is less than the average brightness of the second annular region.

5. The method as recited in claim 1 in which the image parameter is pixel brightness.

6. The method as recited in claim 2 in which the filtering performs at least one of the following operations on the ultrasound image: speckle reduction; edge enhancement; functional feature extraction; or texture feature extraction.

7. The method as recited in claim 1 in which the boundary of the tumor is located in step a) by manually designating a plurality of locations on the image and connecting the designated locations with lines that locate the tumor boundary.

8. The method as recited in claim 1 in which the boundary of the tumor is located in step a) by manually designating a plurality of locations on the image and locating the tumor boundary using the designated locations and an energy-minimizing snake process.

9. The method as recited in claim 1 which includes:
e) displaying an indication that the halo is present.

10. A system for indicating the presence of a halo surrounding an ultrasound image of a tumor, which comprises:
a display for displaying said ultrasound image;
means for identifying the tumor in the displayed ultrasound image and for locating its boundary;
means for defining an inner annulus region of the displayed ultrasound image which surrounds the located boundary of the tumor;
means for defining an outer annulus region of the displayed ultrasound image which surrounds the inner annulus region;
processor means for comparing image parameters in the inner annulus region with image parameters in the outer annulus region to determine the presence of a halo; and
means responsive to the processor means for indicating the presence of a halo.

11. The system as recited in claim 10 in which the means for identifying the tumor includes a mouse for moving a cursor on the display to designate a plurality of points on the tumor image boundary.

12. The system as recited in claim 10 in which the means for identifying the inner annulus region includes a stored value which indicates the number of pixels the inner annulus region extends outward from the located tumor boundary.

13. The system as recited in claim 12 in which the means for identifying the outer annulus region includes a stored second value which indicates the number of pixels the second annulus region extends outward from the inner annulus region.

14. The system as recited in claim 13 in which the second stored value is greater than twice the first stored value.

15. The system as recited in claim 10 in which the image parameters is brightness of the image pixels and the processor means includes:
means for dividing the inner and outer annulus regions into sectors which extend around the image of the tumor; and
means for comparing the average brightness of each inner annulus sector with the average brightness in the corresponding outer annulus sector.

* * * * *